United States Patent [19]

Nguyen et al.

[11] Patent Number: 5,482,644
[45] Date of Patent: Jan. 9, 1996

[54] NONIRRITATING LIQUID DETERGENT COMPOSITIONS

[76] Inventors: Sach D. Nguyen, 167 Sylvan Dr., San Francisco, Calif. 94132; Nguyen Dinh-Nguyen, Lövskogsgatan 18, Göteborg, Sweden

[21] Appl. No.: 394,743

[22] Filed: Feb. 27, 1995

[51] Int. Cl.$^6$ .................................. C11D 9/00; C11D 9/22
[52] U.S. Cl. .................... 252/122; 252/132; 252/106; 252/367; 252/DIG. 5; 252/DIG. 14
[58] Field of Search ...................................... 252/122, 132, 252/106, 367, DIG. 5, DIG. 14

[56] References Cited

U.S. PATENT DOCUMENTS

| | | | |
|---|---|---|---|
| 4,387,040 | 6/1983 | Straw | 252/368 |
| 4,430,245 | 2/1984 | Beattie | 252/117 |
| 4,490,280 | 12/1984 | Joshi et al. | 252/368 |
| 4,839,080 | 6/1987 | Jungermann et al. | 252/107 |
| 4,839,089 | 6/1989 | Shimizu | 252/183.11 |
| 5,227,161 | 7/1993 | Kessler | 252/173 |
| 5,234,618 | 8/1993 | Kamegai et al. | 252/106 |
| 5,236,614 | 8/1993 | Jacquet et al. | 252/96 |
| 5,244,666 | 9/1993 | Murley | 252/107 |
| 5,262,079 | 11/1993 | Kacher et al. | 252/117 |
| 5,290,471 | 3/1994 | Greene et al. | 252/108 |
| 5,308,526 | 5/1994 | Dias et al. | 252/125 |
| 5,334,388 | 8/1994 | Hoang et al. | 424/402 |
| 5,352,389 | 10/1994 | Gazzani | 252/544 |
| 5,366,653 | 11/1994 | Cooring | 252/135 |

FOREIGN PATENT DOCUMENTS 15666  9/1992  WIPO .

*Primary Examiner*—Paul Lieberman
*Assistant Examiner*—Michael P. Tierney
*Attorney, Agent, or Firm*—L. Arnold Thaxton

[57] ABSTRACT

The present invention relates to nonirritating, environmentally friendly, and aqueous detergent compositions suitable in the removal of numerous unwanted deposits from a wide range of substrates. Selectively, a fragrant material can be added to these compositions rendering them adequate as a skin degreaser for users who perform work on oily and/or greasy machine parts. Similarly, a chemotherapeutic agent and a fragrant material may be added to these compositions making them effective as a presurgical scrub for surgeons. Further, a vegetable oil, such as sweet-scented sunflower oil containing vitamin E and rich in unsaturated glycerides, may be added, in a minuscule amount, to these compositions to produce a very light-fatted soap.

7 Claims, No Drawings

NONIRRITATING LIQUID DETERGENT COMPOSITIONS

FIELD OF THE INVENTION

This invention pertains to heavy duty liquid detergent compositions. These detergents are useful in removing oil, grease and unwanted deposits—including traces of heavy metals—on skin surface, and generally, the removal of unwanted deposits from objects ranging from porously soft fabrics to rigidly hard metals.

BACKGROUND OF THE INVENTION

Any trip to a hardware or automotive supply store provides one with the appreciation that numerous detergents are available for all sorts of cleaning purposes. A few of these detergents are useful as multi-purpose cleaners, while most appear to have been developed for removal of a particular deposit from a specific substrate. Both for convenience and economic reasons, it is acknowledged in the art that consumers are desirous of a multi-purpose liquid detergent capable of removing a variety of unwanted deposits from a variety of materials, surfaces, and human skin.

It is also acknowledged in the art that liquid detergents exhibit an appreciable advantage over powdered detergents because the former can be applied to a substrate in a concentrated and uniform manner.

As regards hard surfaces, it is often preferable to remove oil or grease therefrom prior to making repairs, i.e. machinery or automotive parts. There are many occasions when it is necessary to remove unwanted deposits from soft materials such as clothing, leather, and athletic shoes. There are other moments when one may desire to remove incrustation (scales) from the outer hull of a boat or valve mechanism, both of which, having been exposed to sea water. Moreover, there are many occasions when an automobile mechanic wishes to degrease his hands or a surgeon wishes to scrub prior to surgery with a nonirritating detergent demonstrative of superior dermal compatibility.

It is known in the art that some existing detergent compositions have been environmentally objectionable. Contrariwise, these related water-based detergents are biodegradable and environmentally appropriate.

Various prior art patents that relate to the subject matter of this invention, and pertaining to a form of liquid detergent, embraces the U.S. Pat. No. 4,430,245 and issued to I. Beattie. As can be seen, the Beattie patent teaches an enabling means to an aqueous liquid soap composition comprising a mono- and diethanolamine soap and a thickening agent selected from $C_{12}$ to $C_{18}$ fatty acids and/or $C_{12}$ to $C_{18}$ fatty acid alkanolamides. These compositions are useful as personal or fabric cleaners.

The patent to F. Jacquet et al., U.S. Pat. No. 5,236,614, describes microemulsions, as all-purpose cleaning compositions, that remove oil, grease, and others, such as soils from dishes, appliances, woodwork, heating ducts, grills, clothing, and mildew. It can be seen that the patented microemulsions contain an alkali metal hypochloride and a sodium paraffin sulfonate.

The patent to J. Kamegai et al., U.S. Pat. No. 5,234,618, discloses a liquid cleaner containing the essential ingredients of (1) a saccharide non-ionic surfactant, (2) an antibacterial agent, and (3) a detergent composition. These cleaners exhibit antidandruff and high antibacterial effects when used as a body detergent.

The patent to J. Kessler, U.S. Pat. No. 5,227,161, defines an epidermal cleaner for disinfecting pathogens at skin surface, wherein the cleaner contains peroxidase and a source of peroxide and iodide.

It is in light of the above art background that investigative efforts, by the present co-inventors, have led to the claimed new and improved nonirritating liquid detergents. None of the prior art compositions, either separately or in union, are seen to teach the claimed liquid detergent compositions which (1) generally removes oil, grease and soil deposits from soft and hard surfaces, (2) removes incrustation from hard surfaces, (3) is an antiseptic and nonirritating skin cleaner, (4) is environmentally acceptable, and (5) displays a stable and long shelf life.

It is therefore an object of the present invention to provide water-based, biodegradable, environmentally friendly, synergistic cleaning compositions that exhibit use in removing a large range of unwanted deposits from a broad range of objects.

A related object of the invention is to provide an all-purpose and synergistically effective liquid detergent composition.

Another object of the present invention is to provide a stable liquid detergent that is capable of removing oil, grease, soil deposits, and incrustation from objects disposed to marine conditions, such as sea-going vessels and their parts.

Yet another object of this invention is to combine a chelating agent with the liquid detergents in order to bind and remove traces of heavy metals, such as chromium, nickel, lead, and mercury, since some of which have the ability of penetrating the skin into the blood circulation.

A further object of the invention is to combine a chemotherapeutic agent with the liquid detergents to disinfect microbial agents as the detergents clean and degrease the skin.

A still further object of this invention is to provide related compositions that are nonirritating, nontoxic, cost effective, convenient to use, and stable in long storage.

SUMMARY OF THE INVENTION

The present invention is directed to an aqueous and multi-purpose or general use detergent composition comprising a synergistic mixture of: potassium and sodium salts of fatty acids, glycerol, isopropanol, sodium propionate, citric acid and its potassium and sodium salts, ethylenediaminetetraacetic acid disodium salt (EDTA), butylated hydroxytoluene (BHT), and water. The foregoing compositional arrangement provides a base soap, to which can be added a fragrant or perfume material as well as a chemotherapeutic agent, i.e. Irgasan®, for a skin-cleansing detergent. A minimal quantity of fat, such as sunflower oil, can also be added to the base formulation in order to yield a light-fatted soap.

DETAILED DESCRIPTION OF THE INVENTION

There are two basic and closely related formulations to this invention, each of which is useful for cleaning a wide range of substrate materials from unwanted deposits thereon. Each formulation provides a soap base A and soap base B, respectively; however, both formulations are concentrated aqueous solutions containing potassium and sodium salts of selected fatty acids (deriving from a selected fat), glycerol, isopropanol, sodium propionate, citric acid and its potassium and sodium salts, EDTA disodium salt, BHT, and purified water. The fats appropriate for manufacturing the soap base A, which is suitable for washing with soft water as well as sea water, are those composing a high proportion of glycerides of medium-chain ($C_{12}$ to $C_{14}$) fatty acids, such as coconut oil, palm-kernel oil and bassu-kernel oil, or of glycerides of hydroxy fatty acids in the castor oil. Whereas, the fats suitable for producing the soap base B are those composed of glycerides of the long-chain ($C_{16}$ to $C_{18}$) fatty acids, such as sunflower oil, soybean oil, corn oil, groundnut oil, palm oil, lard, and tallow.

Experimentation promotes the observation that purified water, such as softened, deionized, and filtered, is significant and preferred in assemblying the hereinabove formulations.

The above combination of components operate synergistically to a degree of efficacy that goes beyond already known soap compositions used on a wide range of substrates.

Each soap base is benign and show no deleterious affect on the substrate material to which either base is applied or to individuals who are exposed to it. In kindred manner, these soap bases are environmentally acceptable and biodegradable under the rigorously applied laws and regulations. The biodegradable components show no tendency to leave harmful residues in soils, water, or air.

The above soap bases, for which a greater detailed discussion will be set forth below, are useful either alone or in slightly modified formulations in removing oil, grease, dirt including traces of toxic heavy metals, stains, scales from marine exposed objects, and other unwanted (soiled) deposits from clothing, household fabrics, athletic shoes, leather, upholstery, machinery parts, and the user's skin. Importantly, these soap bases themselves or in slightly modified formulations do not stain the substrates from which they are intended to remove unwanted deposits, after said substrates are rinsed with water.

Two separate processes of saponification are used to manufacture the soap bases of this invention, and both processes are art reknown. Exemplary, Example I discloses the means to preparing soap base A by a cold process. Example II discloses a means of producing soap base B by means of a semi-boiled technique.

The basic formulation for soap base A is an aqueous solution consisting essentially of the following components, all expressed as parts by weight.

EXAMPLE I

| Soap Base A | |
|---|---|
| Ingredients | Parts by Weight |
| Coconut Oil (Saponification value 244) | 15.02 |
| Potassium Hydroxide (87.9%) | 2.92 |
| Sodium Hydroxide (98.1%) | 0.80 |
| Isopropanol (99.0%) | 4.68 |
| Purified Water | 27.34 |
| Anhydrous Sodium Propionate | 0.10 |
| EDTA-Disodium Salt | 0.05 |
| Anhydrous Citric Acid | 0.20 |
| Butylated Hydroxytoluene (BHT) | 0.0014 |

In carrying out the process to produce soap base A, some of the ingredient are first and separately dissolved in purified water, above described, where:

Potassium hydroxide is dissolved in 8.55 parts water,

Sodium hydroxide is dissolved in 2.61 parts water,

Sodium propionate is dissolved in 1.0 part water,

EDTA-disodium salt is dissolved in 1.0 part water, and

Citric acid is dissolved in 1.0 part water.

These water parts, about 14.16 in all, are included in the above quantity of purified water shown as 27.34 parts of the graphic base A formulation. By way of an important observation, it deserves noting that (1) weight of reactant/ingredients, one to the other, and (2) lineal order of reactant/ingredients are critical to a successful product herein. The concentration of caustic alkali in each lye is about 30%. The solution of BHT is made by dissolving this antioxidant in 0.01 part by weight of isopropanol.

In the process of producing soap base A, the full amount of coconut oil and of isopropanol are first placed in a soap crutcher, which is a water jacketed vessel equipped with a motor and agitator baffle, such as made by Hanson & Edwards, Ltd., T/A Scun Thorp of the United Kingdom. The temperature of the mixture is maintained at 35 to 40 degrees celsius. The agitator is engaged, and one-half the amount of KOH solution is run into the fatty blend. The mixture, that is rapidly crutched, begins to thicken marking the inaugural of the saponification process between fat and alkali. This exothermic reaction raises the temperature to about 65 to 75 degrees Celsius, where it is carefully held while the remainder solution of KOH and all that of NaOH are gently and successively introduced to the mixture being agitated. The partial soap formed becomes very thick. The remaining purified water, 13.18 parts by weight, warmed to 65 to 70 degrees Celsius, is poured into the reaction vessel, whereupon the thick mass of soap becomes a viscous solution. The temperature of the reaction mixture continues to fall, indicating completion of the saponification. The pH value of the crude soap is observed to be at 8 or 9. Solutions of sodium propionate and EDTA are run into the soap, thereafter the citric-acid solution is gently added to adjust the pH value to neutral (pH 7). Lastly, the BHT solution is added to the crutcher and the final soap base allowed to cool.

As earlier indicated, soap base B is produced via a semi-boiled technique, albeit similar to the noted cold process, exception directed to a need for a higher temperature to facilitate initiating the saponification reaction itself. The semi-boiled process is determined to be more suitable in manufacturing soaps from fats containing an important proportion of glycerides of long-chain fatty acids, those possessing more than 14 carbon atoms, as already mentioned above.

The basic composition for soap base B is an aqueous solution, similar to soap base A, and consists essentially of the following components expressed in parts by weight.

EXAMPLE II

| Soap Base B | |
|---|---|
| Ingredients | Parts by Weight |
| Sunflower Oil (Saponification value 189) | 12.00 |
| Potassium Hydroxide (87.9%) | 1.81 |
| Sodium Hydroxide (98.6%) | 0.50 |
| Isopropanol (99.0%) | 3.95 |
| Purified Water | 22.00 |
| Anhydrous Sodium Propionate | 0.08 |
| EDTA-Disodium Salt | 0.04 |
| Anhydrous Citric Acid | 0.12 |

-continued

Soap Base B

| Ingredients | Parts by Weight |
| --- | --- |
| BHT | 0.0024 |

As in the cold process of manufacture, some of the following ingredients are first and separately dissolved in purified water:

Potassium hydroxide is dissolved in 6.02 parts of water,

Sodium hydroxide is dissolved in 1.62 parts of water,

Sodium propionate is dissolved in 0.40 parts of water,

EDTA-disodium salt is dissolved in 0.80 parts of water, and

Citric acid is dissolved in 0.06 parts of water.

These parts of water, about 9.44 in all, are included in that shown above as 22.00 parts; remaining water is thus, at 12.56 parts. The concentration of caustic alkali in each lye is about 30%.

The fatty material, isopropanol, and crystalline BHT are first placed into the crutcher where the temperature is held at 65 to 70 degrees Celsius. The ensuing preparation of soap base B is conducted in the same manner as set forth is producing soap base A hereinabove.

It is noted that 1.0 part of fatty oil can be converted into 3.2 to 3.4 parts of a liquid soap containing 30.5 to 32.0% potassium and sodium carboxylates, having a density of about 1.08 at 20 degrees Celsius.

Each of soap bases A and B can be used to prepare variant liquid soaps as described below.

EXAMPLE III

| Ingredients | Parts by Weight |
| --- | --- |
| Soap base A or B | 100.00 |
| Sunflower Oil | 0.002 |
| Fragrance (optional) | 0.2 to 0.4 |

The above formulation demonstrates superior cleaning properties as a general purpose type detergent, and that made from the soap base A is a marine soap.

After either of soap A or B has been permitted to cool in the reaction vessel, sunflower oil and fragrance are admitted while gently agitating the mixture.

EXAMPLE IV

| Ingredients | Parts by Weight |
| --- | --- |
| Soap base A or B | 100.00 |
| Irgasan ®:Isopropanol | 0.40:0.80 |
| Sunflower Oil | 0.002 |
| Fragrance (optional) | 0.2 to 0.4 |

It has been found that this detergent composition is an excellent skin cleaner, particularly as a medical or presurgical skin scrub, and that made from the soap base A is a marine soap. Irgasan® must be dissolved in isopropanol prior to its introduction to either soap base A or B within the crutcher. Further, it is preferred that the isopropanolic solution of Irgasan®, and fragrance are run into the selected soap base and maintained at a crutcher temperature of 25 to 35 degrees Celsius.

In terms of the medical scrub, the approximate percentage of components may be expressed as:

| | |
| --- | --- |
| Potassium and sodium carboxylates | 31.50% |
| Water | 54.40 |
| Isopropanol | 9.80 |
| Glycerol | 3.00 |
| Sodium propionate | 0.20 |
| Sodium and potassium citrates | 0.30 |
| EDTA-disodium salt | 0.10 |
| BHT | 0.006 |
| Irgasan ® | 0.40 |
| Fragrance (perfume) | 0.20 to 0.30 |

In the interest of being full, clear and exact in defining this invention, a brief discussion, as regards those ingredients which are not immediately discerned in their indigenous function, appears to be properly serving. Sodium propionate exhibits some antibiotic activity and functions as a skin protector. BHT is a very useful antioxidant and promotes the shel-life of these compositions. Isopropanol operates, in the inventive compositions, as a topical disinfectant, keeps the soaps aseptic, and reduces the dermal bacteria count. EDTA-disodium salt acts as a chelating agent binding and removing traces of heavy metals as chromium, nickel, lead, and mercury to name a few. Irgasan®, as previously announced, is a chemotherapeutic agent and is included in the medical scrub composition to further and completely destroy any skin disposed microorganisms.

This invention, having been fully described, is not limited to the embodiments set forth in the description which is given by way of example in practicing the best mode contemplated and not to limit the invention thereof, while such limitations are applicable in accordance with the scope of the appended claims.

We claim:

1. An aqueous detergent composition, wherein the ingredients are expressed in parts by weight, that consisting essentially of a fat material selected from the group consisting of coconut oil, palm-kernel oil, babassu oil, and castor oil at 15.02 parts, wherein the fat has a saponification value of 244;

potassium hydroxide at 2.92 parts (for 87.9% KOH) in aqueous solution;

sodium hydroxide at 0.80 parts (for 98.6% NaOH) in aqueous solution;

sodium propionate at 0.10 parts in aqueous solution;

ethylenediamine tetraacetic acid (EDTA) disodium salt at 0.05 part in aqueous solution;

citric acid at 0.20 part in aqueous solution;

butylated hydroxytoluene (BHT) at 0.0014 part in isopropanol;

isopropanol at 4.68 parts; and purified water at 13.18 parts.

2. The invention of claim 1, wherein said fat material is coconut oil.

3. A modified composition consisting essentially of the composition of claim 1, and in addition, 0.002 part by weight of sunflower oil and 0.2 to 0.4 parts by weight of a fragrant material.

4. An aqueous detergent composition, wherein the ingredients are expressed in parts by weight, that consisting essentially of:

a fat material selected from the group consisting of sunflower oil, soybean oil, corn oil, groundnut oil, palm oil, lard, and tallow at 12.00 parts, wherein the fat has a saponification value of 189;

potassium hydroxide at 1.81 parts (for 87.9% KOH) in aqueous solution;

sodium hydroxide at 0.50 parts (for 98.6% NaOH) in aqueous solution;

sodium propionate at 0.08 parts in aqueous solution;

ethylenediamine tetraacetic acid (EDTA) disodium salt at 0.04 part in aqueous solution;

citric acid at 0.12 part in aqueous solution;

butylated hydroxytoluene (BHT) at 0.0024 parts;

isopropanol at 3.95 parts; and purified water at 12.56 parts.

5. The invention of claim 4, wherein said fat material is sunflower oil.

6. A modified composition consisting essentially of the composition of claim 4, and in addition, 0.002 part by weight of sunflower oil 0.2 to 0.4 parts by weight of a fragrant material, and 0.4 part Irgasan® dissolved in 0.8 part by weight of isopropanol.

7. A modified composition consisting essentially of the composition of claim 1, and in addition, 0.002 part by weight of sunflower oil, 0.2 to 0.4 parts by weight of a fragrant material, and 0.4 part Irgasan® dissolved in 0.8 part by weight of isopropanol.

* * * * *